United States Patent
Groleau

(10) Patent No.: US 6,329,364 B1
(45) Date of Patent: Dec. 11, 2001

(54) CRYSTALLINE FORM OF DIHYDRO-2,3-BENZODIAZEPINE DERIVATIVE

(75) Inventor: Edward G. Groleau, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/412,242

(22) Filed: Mar. 28, 1995

Related U.S. Application Data

(63) Continuation-in-part of application No. 08/298,645, filed on Aug. 31, 1994, now abandoned.

(51) Int. Cl.[7] .................... A61K 31/551; C07D 491/056
(52) U.S. Cl. ............................................. 514/220; 544/557
(58) Field of Search .................... 514/220, 557; 540/557

(56) References Cited

U.S. PATENT DOCUMENTS 5,459,137  10/1995  Andrasi et al. ...................... 514/220

FOREIGN PATENT DOCUMENTS

| 0492485 | 7/1992 | (EP) . | |
|---|---|---|---|
| 2194236 | * 3/1988 | (GB) | ...................................... 540/557 |
| WO 95/01357 | 1/1995 | (WO) . | |

OTHER PUBLICATIONS

Ling, et. al., J. Chem. Soc. Perkin Trans., vol. 1, pp 1423–1427, 1995 "Asymmetric reduction of a carbon–nitrogen double bond: enantioselective synthesis of 4,5–dihydro–3H–2,3–benzodiazepines".

Tarnawa et. al., Bioorganic and Medicinal Chemistry Letters, vol. 3, No. 1, pp 99–104, 1993.

* cited by examiner

Primary Examiner—Richard L. Raymond
(74) Attorney, Agent, or Firm—Nelsen L. Lentz

(57) ABSTRACT

A physical form of (R)-7-acetyl-5-(4-aminophenyl)-8,9-dihydro-8-methyl-7H-1,3-dioxolo[4,5-h][2,3]benzodiazepine having an X-ray powder diffraction pattern with d spacings at 12.78, 9.48, 8.99, 8.64, 8.23, 6.39, 6.27. 5.73, 4.01 and 3.96 Å. The compound is useful as an AMPA antagonist.

3 Claims, No Drawings

CRYSTALLINE FORM OF DIHYDRO-2,3-BENZODIAZEPINE DERIVATIVE

This application is a continuation-in-part of U.S. patent application Ser. No. 08/298,645 filed on Aug. 31, 1994, now abandoned.

FIELD OF THE INVENTION

This invention relates to a novel physical form of a dihydro-2,3-benzodiazepine derivative useful as a pharmaceutical in the treatment of disorders of the nervous system.

BACKGROUND OF THE INVENTION

European patent application publication number EP-A1-0492485 discloses the compound 1-(4-aminophenyl)-3-acetyl-4-methyl-7,8-methylenedioxy-3,4-dihydro-5H-2,3-benzodiazepine. The compound is a potent and selective antagonist of the excitatory amino acid AMPA receptor and is believed to have the ability to treat a variety of neurological disorders. The (R)-enantiomer of this compound hereinafter referred to as (R)-7-acetyl-5-(4-aminophenyl)-8,9-dihydro-8-methyl-7H-1,3-dioxolo[4,5-h][2,3]benzodiazepine, is the most potent enantiomer.

SUMMARY OF THE INVENTION

The present invention provides a physical form of (R)-7-acetyl-5-(4-aminophenyl)-8,9-dihydro-8-methyl-7H-1,3-dioxolo[4,5-h][2,3]benzodiazepine having an X-ray powder diffraction pattern with d spacings at 12.78, 9.48, 8.99, 8.64, 8.23, 6.39, 6.27, 5.73, 4.01 and 3.96 Å. It also provides a process for producing this form, pharmaceutical compositions containing it and methods of using it.

DETAILED DESCRIPTION OF THE INVENTION

It has been found that (R)-7-acetyl-5-(4-aminophenyl)-8,9-dihydro-8-methyl-7H-1,3-dioxolo[4,5-h][2,3]benzodiazepine is polymorphic.

The first physical form of (R)-7-acetyl-5-(4-aminophenyl)-8,9-dihydro-8-methyl-7H-1,3-dioxolo[4,5-h][2,3]benzodiazepine to be found had a melting point of about 168–172° C. and an X-ray powder diffraction pattern with characteristic d spacings at 6.57 and 5.24 Å. This physical form is referred to hereinafter as form I. It has been prepared by reducing (R)-7-acetyl-8,9-dihydro-8-methyl-5-(4-nitrophenyl)-7H-1,3-dioxolo[4,5-h][2,3]benzodiazepine in ethanol using hydrogen and palladium on carbon as catalyst, then removing the catalyst by filtration, evaporating off the ethanol, heating the residue in 5.7 volumes of 1:1 water/ethanol under reflux and then allowing the resultant solution to cool.

Surprisingly, modifying the process used to prepare form I by using ammonium formate and palladium on carbon instead of hydrogen and palladium on carbon gave a new physical form of (R)-7-acetyl-5-(4-aminophenyl)-8,9-dihydro-8-methyl-7H-1,3-dioxolo[4,5-h][2,3]benzodiazepine, hereafter referred to as form II. Thus form II has been prepared by reducing (R)-7-acetyl-8,9-dihydro-8-methyl-5-(4-nitrophenyl)-7H-1,3-dioxolo[4,5-h][2,3]benzodiazepine in ethanol using ammonium formate and palladium on carbon as catalyst, then removing the catalyst by filtration, evaporating off the ethanol, heating the residue in 6 volumes of 1:1 water/ethanol under reflux, and allowing the resultant solution to cool. Form II has been found to have an X-ray powder diffraction pattern with characteristic d spacings at 13.12 and 5.01 Å.

Modifying the process used to prepare form II by using potassium formate and palladium on carbon instead of ammonium formate and palladium on carbon surprisingly gave yet another physical form, referred to hereinafter as form III. Thus form III has been prepared by reducing (R)-7-acetyl-8,9-dihydro-8-methyl-5-(4-nitrophenyl)-7H-1,3-dioxolo[4,5-h][2,3]benzoclazepine in ethanol using potassium formate and palladium on carbon as catalyst, then removing the catalyst by filtration, evaporating off the ethanol, heating the residue in 6 volumes of 1:1 water/ethanol under reflux and allowing the resultant solution to cool. Form III has been found to have an X-ray powder diffraction pattern with characteristic d spacings at 10,61, 8.83, 6.78, 5.83, 4.13 and 3.74 Å. This physical form is the subject of a co-pending patent application (ref. X9386C).

Surprisingly, yet another physical form, hereinafter referred to as form IV has also been found. This form was initially observed to have been formed after form II had been heated. It was subsequently found that form IV may be prepared directly by modifying the process used to prepare form III, in particular by increasing the volume ratio of water/ethanol used in the crystallization step. Thus form IV has been prepared by reducing (R)-7-acetyl-8,9-dihydro-8-methyl-5-(4-nitrophenyl)-7H-1,3-dioxolo[4,5-h][2,3]-benzodiazepine in ethanol using potassium formate and palladium in carbon as catalyst, then removing the catalyst by filtration, evaporating off the ethanol, heating the residue in 8 volumes of 5:3 water/ethanol or 7 volumes of 4:3 water/ethanol under reflux, optionally seeding with Form IV crystals at 70–80° and allowing the resultant mixture to cool. Form IV has been found to have an X-ray powder diffraction pattern with characteristic d spacings at 12.78, 9.48, 8.99, 8.64, 8.23, 6.39, 6.27, 5.73, 4.01 and 3.96 Å. This physical form is provided as one aspect of the invention.

Form I has been found to possess several disadvantageous properties. In particular, it has been found to crystallize out as a thick slurry which is difficult to stir and transfer. The filtration time has been found to be unacceptably long for large scale production, and the drying time for filtered wet cake is also long. Furthermore, Form I has been found to be thermally unstable, and has been found to convert to form IV or, occassionally, yet another physical form hereinafter referred to as form V. Form V has been found to have an X-ray powder diffraction pattern with characteristic d spacings at 6.12, 5.94 and 5.48 Å. Form V shows multiple phase transitions when subject to differential scanning calorimetry.

Form II has been found to crystallize out as a stirrable suspension which can readily be filtered. However, it has been found to dry slowly and to retain crystallization solvent. Like Form I, it has been found to be thermally unstable with regard to conversion to form IV.

Form III has been found to crystallize out as a stirrable suspension which can readily be filtered and dried. It has also been found to be thermally stable.

Form IV has also been found to crystallize out as a stirrable suspension which can readily be filtered and dried. Like Form III, it has also been found to be thermally stable.

Each of Forms I, II, III, IV and V has been characterized by a X-ray diffraction, by $^{13}C$ solid state NMR spectroscopy and by differential scanning calorimetry. The techniques used, and the physical characteristics determined for samples of each form are given below, together (for forms III and IV only) with general ranges obtained by differential scanning calorimetry using a number of different samples.

X-ray diffraction (XRD) patterns were obtained on a Siemens D5000 X-ray diffractometer, equipped with a Cu Kα (λ=1.54056 Å) source operating at a tube load of 50 KV and 40 mA. Data was collected with a Kevex solid-state detector. Each sample was scanned between 4 and 35° 2 θ with a step size of 0.03° and a maximum scan rate of 2 sec/step.

Differential scanning calorimetry (DSC) measurements were performed on a geiko differential scanning calorimeter. Samples (2–5 mg) sealed in aluminum pans were heated from ambient (25° C.) to at least 200° C. at a rate of 10° C./min.

$^{13}C$ Cross polarization/magic angle spinning (CP/MAS) NMR spectra were obtained using a Varian Unity 400 MHz spectrometer operating at a carbon frequency of 100.577 MHZ and equipped with a complete solids accessory and Varian 5 or 7 mm VT CP/MAS probe. Typical measurement conditions were as follows: 90(deg) proton r.f. pulse 5.0 ms, contact time 1–2 ms, pulse repetition time 5s, MAS frequency 7 kHz, spectral width 50 kHz, and acquisition time 50 ms. the chemical shifts were referenced to the $CH_3$ group of hexamethylbenzene (delta=17.3 ppm) by sample replacement.

Form I
DSC: Major endotherm at 171.5° C., minor endotherm at 207.4° C.
XRD:

| Spacing, d (Å) | Relative intensity |
|---|---|
| 17.30 | 100 |
| 12.28 | 34 |
| 7.76 | 71 |
| 6.57 | 37 |
| 5.24 | 35 |
| 4.81 | 94 |
| 4.34 | 30 |
| 4.21 | 29 |
| 4.09 | 19 |
| 3.98 | 14 |
| 3.62 | 18 |
| 2.85 | 12 |

Form II
DSC: Endotherm at 85.2° C., exotherm at 91.4° C., endotherm at 192.3° C.
XRD:

| Spacing, d (Å) | Relative intensity |
|---|---|
| 13.12 | 100 |
| 9.72 | 23 |
| 6.73 | 37 |
| 6.61 | 60 |
| 5.25 | 28 |
| 5.01 | 94 |
| 4.89 | 70 |
| 4.75 | 41 |
| 4.24 | 28 |
| 3.74 | 25 |

Form III
DSC: Endotherm at 194.7° C., for this sample. Other samples have been found to show an endotherm at a temperature in the range of from 192 to 195° C.
XRD:

| Spacing, d (Å) | Relative intensity |
|---|---|
| 10.61 | 78 |
| 8.83 | 73 |
| 8.33 | 15 |
| 7.85 | 9 |
| 6.78 | 100 |
| 5.83 | 17 |
| 5.68 | 6 |
| 5.31 | 25 |
| 5.11 | 68 |
| 4.94 | 62 |
| 4.78 | 20 |
| 4.55 | 5 |
| 4.41 | 25 |
| 4.13 | 71 |
| 4.07 | 19 |
| 3.90 | 24 |
| 3.74 | 40 |
| 3.53 | 16 |
| 3.42 | 18 |
| 3.37 | 26 |
| 3.28 | 11 |
| 3.21 | 30 |
| 3.02 | 5 |
| 2.85 | 7 |
| 2.78 | 6 |

Form IV
DSC: Endotherm at 203.2° C. for this sample. Other samples have been found to show an endotherm at a temperature in the range of from 201 to 207° C.
XRD:

| Spacing, d (Å) | Relative intensity |
|---|---|
| 12.78 | 100 |
| 9.48 | 29 |
| 8.99 | 17 |
| 8.64 | 23 |
| 8.23 | 59 |
| 6.53 | 58 |
| 6.39 | 13 |
| 6.27 | 20 |
| 5.73 | 33 |
| 5.37 | 44 |
| 5.22 | 14 |
| 5.18 | 11 |
| 5.10 | 15 |
| 4.95 | 32 |
| 4.89 | 61 |
| 4.75 | 12 |
| 4.56 | 10 |
| 4.41 | 29 |
| 4.32 | 20 |
| 4.01 | 53 |
| 3.96 | 35 |
| 3.77 | 22 |
| 3.59 | 31 |
| 3.39 | 15 |
| 3.11 | 19 |

| Form V |  |
|---|---|
| DSC: Endotherm at 170.6° C., exotherm at 177.3° C., endotherm at 206.2° C. | |
| Spacing, d (Å) | Relative intensity |
| 17.37 | 51 |
| 12.29 | 21 |
| 7.75 | 29 |
| 6.79 | 32 |
| 6.12 | 13 |
| 5.94 | 14 |
| 5.48 | 15 |
| 5.34 | 24 |
| 4.89 | 82 |
| 4.33 | 100 |
| 4.26 | 50 |
| 4.08 | 34 |
| 4.02 | 20 |
| 3.65 | 21 |
| 2.86 | 13 |

TABLE I

Solution and Solid-State $^{13}$C NMR Chemical Shift Data.

| Form I | Form II | Form III | Form IV | Form V |
|---|---|---|---|---|
| 176.4 | 173.7 | 175.4 | 174.1, 176.3 | 175.3 |
| 128.6 | 126.9 | 126.3 | 127.5, 129.4 | 148.5 |
| 115.9 | 150.4 | 109.4 | 114.1 | 149.4 |
| 148.9 | 147.6 | 116.1 | 116.3 | 146.7 |
| 146.3 | 134.5 | 149.9 | 148.0, 150.2 | 135.4 |
| 136.4 | 123.3 | 146.0 | 146.4 | 136.7 |
| 123.9 | 129.2 | 135.9 | 136.1 | 151.1 |
| 131.7 | 135.8 | 124.3 | 124.7 | 154.3 |
| 154.5 | 152.1 | 129.1 | 131.2, 133.6 | 155.1 |
| 168.4 | 170.7 | 132.8 | 152.7 | 163.0 |
| 22.2 | 22.2 | 153.5 | 167.7, 169.7 | 167.2 |
| 18.6 | 18.3 | 171.4 | 23.2, 23.7 | 20.6 |
|  |  | 24.3 | 18.5, 19.2 | 19.1 |
|  |  | 19.4 |  | 17.4 |

According to another aspect, the present invention provides a process for the preparation of Form IV, which comprises a) reacting a compound of formula

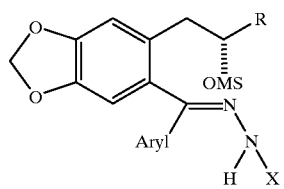

(VII)

in which Ms is methanesulfonyl, R is methyl, X is acetyl and Aryl is p-nitrophenyl with caustic soda to afford a compound of formula I

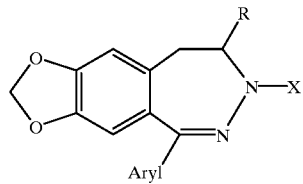

(I)

in which R is methyl, X is acetyl and Aryl is p-nitrophenyl;

b) reducing the p-nitrophenyl group in the formula I compound to an aniline group using potassium formate in the presence of palladium or charcoal as catalyst to afford a compound of formula I in which Aryl is p-aminophenyl; and c) crystallizing the compound of formula I in which Aryl is p-aminophenyl from a mixture of water and ethanol in which the number of volumes of water per volume of ethanol is at least 1.1/1.0.

Step (a) of the process is conveniently performed at a temperature in the range of from 0 to 100° C. Suitable solvents include alkanols such as methanol or ethanol, and ethers such as tetrahydrofuran.

In Step (c), the number of volume of water per volume of ethanol is preferably in the range of from 1.15 to 2.0, more preferably from 1.2 to 1.8 volumes.

The compound of general formula VII may be prepared by a multistep process, starting from a methylenedioxyphenyl ketone derivative. This process comprises:

a) providing a quantity of a compound having the formula:

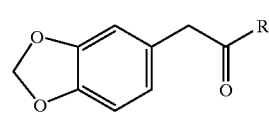

(II)

in which R is methyl;

b) asymmetrically reducing the compound of formula II to yield a compound having the formula:

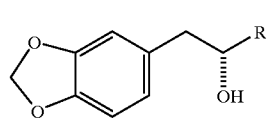

(III)

c) reacting the compound of formula III with p-nitrobenzaldehyde compound of formula Aryl.CHO to yield an isochroman compound having the formula:

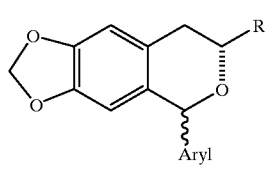

(IV)

d) reacting the compound of formula IV with an oxidizing agent to yield a compound of the formula:

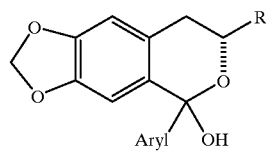

e) reacting the compound of formula V with acetic hydrazide to yield a compound of the formula:

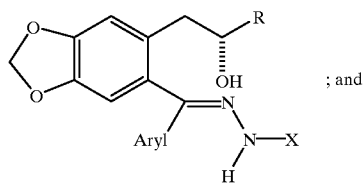

f) reacting the compound of formula VI with methanesulfonyl chloride and a tertiary amine, to form a compound of formula VII.

The preferred process involves the early chiral reduction of a ketone to an alcohol. Substituents are added in a multi-step process to close the benzo-fused pyran ring, before a hydrazine reagent is introduced to open the ring and add the necessary nitrogen components. Finally, the secondary ring is closed by addition of a strong base and the compound is reduced to form the desired compound.

Most preferably, the chiral reduction step is the initial step in the synthesis of the Formula (I) compounds from ketones. The chiral reduction may be effected by use of specific chemicals or, preferably, by using biological agents as disclosed below. Setting the stereochemistry early in the process is beneficial and allows for the later steps to be carried out on relatively enantiomerically pure material. This increases both throughput and enantiomeric purity.

The first step of the process involves a chiral reduction of 3,4- methylenedioxyphenyl acetone to produce a virtually onantiomerically pure alcohol derivative of 1,2-methylenedioxybenzene. Preferably, the enantiomer formed is the S or (+) stereoisomer of the alcohol.

Alternatively, the initial step may involve the combination of a halo derivative of 1,2-methylenedioxybenzene with an enantiomerically enriched epoxide. This also results in the production of a highly enantiomerically enriched alcohol derivative of 1,2-methylenedioxybenzene.

The material used to effect the chiral reduction initial step may be either chemical or preferably biological. In the case of biological agents, the preferred agents are reducing enzymes, most preferred being yeasts from the Zygosaccharomyces group. Other biological agents which may be used include: *Pichia fermentans, Endomycopsis fibuligera, Nematospora coryli,* Saccharomyces sp., *Candida famata, Saccharomyces pastorianus, Saccharomyces cerevisiae, Saccharomyces uvarum, Candida utilis, Saccharomyces globosus, Kluyveromyces dobzhansk, Kluyveromyces lactis, Candida albicans,* bakers' yeast, *Zygosaccharomyces rouxii, Lactobacillus acidophilus, Aureobasidium pullulans, Mortierella isabellina, Rhizopus oryzae, Kloeckeva javanica, Hanseniaspora valbyensis, Octosporomyces octospori, Candida guilliermondi, Candida parapsilosis, Candida tropicalis, Torulopsis taboadae, Torulopsis ethanolitolerans, Torulopsis ptarmiganii, Torulopsis sonorensis, Trigonopsis variabilis, Torulopsis enokii, Torulopsis methanothermo,* SAF instant yeast, ashland yeast inact., *Candida boidinii, Candida blankii* and Red Star yeast.

The desired intermediate formed in the initial step is an alcohol substituted congener of 1,2-methylenedioxybenzene, with the most preferred congener consisting of (S)-α-Methyl-1,3-benzodioxole-5-ethanol.

The desired intermediate compound formed in the initial step is then subjected to a Pictet-Spengler reaction which provides for convergent fusion of the benzodiazepine carbon constituents. The preferred reagent of choice is p-nitrobenzaldehyde, although other reagents known to those skilled in the art such as acetals may be used. The preferred intermediates are dihydrobenzopyrans with the most preferred compound being 7,8-dihydro-7-methyl-5-(4-nitrophenyl)-5H-1,3-dioxolo-benzo[b]pyran.

The dihydrobenzopyran congener is then oxidized at the C5 position to yield a hemiketal derivative of the general formula

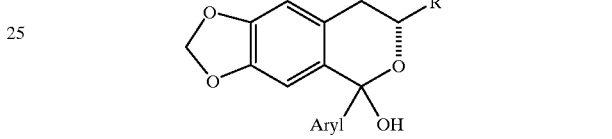

The preferred oxidizing agents include potassium permanganate, DDQ (2,3-dichloro-5,6-dicyano-1,4-benzoquinone) or others, with the most preferred agent being a sodium hydroxide and air combination.

The C5-hemiketal is then reacted with acetic hydrazide in the presence of acid in order to form the hydrazone intermediate. In this step, the benzopyran ring is opened such that the hydrazone component is attached to the C5 carbon, The reaction is conveniently performed in a refluxing aromatic or protic solvent, with the preferred hydrazone being of the general formula

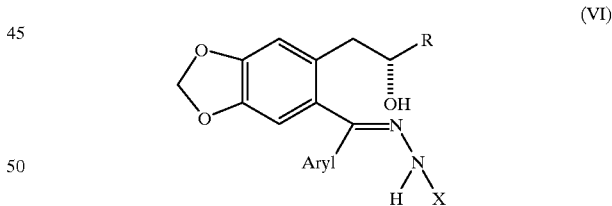

wherein R is $CH_3$, X is acetyl and Aryl is p-nitrophenyl.

The process can be summarized by the following Schemes.

Scheme (I)

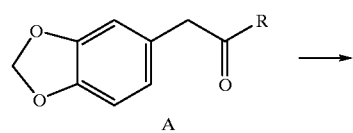

-continued

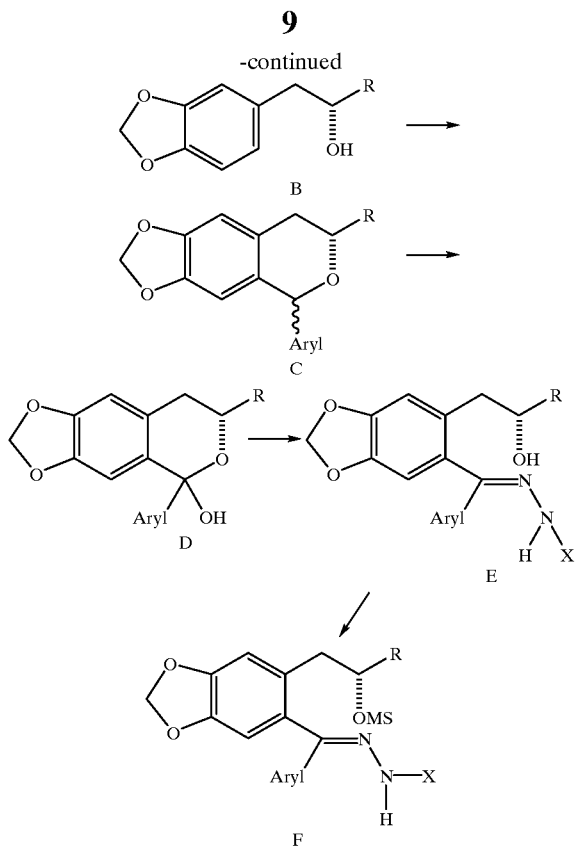

In scheme (I), the initial step of the process involves the addition of biological agents, most preferably *Zygosaccharomyces rouxii*, to reduce the ketone to the desired alcohol. A suitable quantity of an adsorbent resin such as AD-7, XAD-7, HP2MGL (cross-linked polymethacrylates from Rohm & Haas), HP20 (polystyrenic), or SP207 (brominated polystyrene from Mitsubishi) may be added to the reaction mixture to prevent death of the organism and to adsorb the alcohol as it is formed. Other similar resins may also be used.

SCHEME II

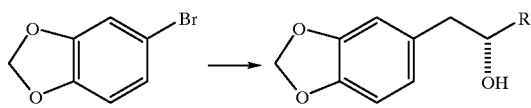

In scheme (II), the initial step of the process involves reacting an aryl halide derivative, such as 4-bromo-1,2 (methylenedioxy) benzene, with an alkali metal hydrocarbon (sec-butyllithium is preferred) and an enantiomerically pure epoxide. Alternatively, an aryl halide may first be converted into a Grignard reagent by reaction with magnesium, then reacted with an enantiomerically pure epoxide in the presence of Copper (I) iodide as catalyst. Preferred is (S)-(−)-propylene oxide. In both scheme (I) and scheme (II), the objective is to set the stereochemistry of the C8 atom of the benzodiazepine ring as early as possible. Both schemes have been observed to accomplish this objective and have formed enantiomerically enriched (ee) alcohols in the 98% purity range.

(R)-7-acetyl-5-(4-aminophenyl)-8,9-dihydro-8-methyl-7H-1,3-dioxolo[4,5-h][2,3]benzodiazepine is known to be a selective antagonist for the AMPA receptor. According to yet another aspect, therefore, the present invention provides a method of blocking AMPA receptors in a mammal requiring such treatment, which comprises administering an effective amount of Form IV.

A variety of physiological functions have been shown to be subject to influence by excessive or inappropriate stimulation of excitatory amino acid neurotransmission. (R)-7-Acetyl-5-(4-aminophenyl)-8,9-dihydro-8-methyl-7H-1,3-dioxolo[4,5-h][2,3]benzodiazepine is believed to have the ability to treat a variety of neurological disorders in mammals associated with this condition which include acute neurological disorders such as cerebral deficits subsequent to cardiac bypass surgery and grafting, stroke, cerebral ischemia, spinal cord trauma, head trauma, perinatal hypoxia, cardiac arrest and hypoglycemic neuronal damage. The compound is believed to have the ability to treat a variety of chronic neurological disorders such as Alzheimer's Disease, Huntington's Chorea, amyotrophic lateral sclerosis, AIDS-induced dementia, ocular damage and retinopathy, and idiopathic and drug-induced Parkinson's Disease. The present invention also provides methods for treating these disorders which comprise administering to a patient in need thereof an effective amount of form IV.

The compound is also believed to have the ability to treat a variety of other neurological disorders in mammals that are associated with glutamate dysfunction including muscular spasms, convulsions, migraine headaches, urinary incontinence, psychosis, drug tolerance and withdrawal, anxiety, emesis, brain edema, chronic pain, and tardive dyskinesia. The compound is also useful as an analgesic agent. Therefore, the present invention also provides methods for treating these disorders which comprise administering to a patient in need thereof an effective amount of form IV.

The term "effective amount" is used herein to represent an amount of form IV which is capable of blocking the AMPA excitatory amino acid receptor. The particular dose of compound administered according to this invention will of course be determined by the particular circumstances surrounding the case, including the compound administered, the route of administration, the particular condition being treated, and similar considerations. The form can be administered by a variety of routes including the oral, rectal, transdermal, subcutaneous, intravenous, intramuscular, or intranasal routes. Alternatively, the form may be administered by continuous infusion. A typical daily dose will contain from about 0.01 mg/kg to about 30 mg/kg of the active compound of this invention. Preferred daily doses will be about 0.05 mg/kg to about 24 mg/kg, more preferably about 0.1 to about 20 mg/kg.

Form IV will generally be administered in a pharmaceutical composition. According to another aspect, the present invention provides a pharmaceutical composition, which comprises form IV and a pharmaceutically acceptable diluent or carrier.

In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of, for example, tablets, pills, powders, lozenges, sachets, cachets, suspensions, aerosols, soft and hard gelatin capsules and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, methyl cellulose, methyl and propyl hydroxybenzoate, talc, magnesium sterate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed release of the active ingredient after administration to the patient by employing procedures well known in the art.

The compositions are preferably formulated in a unit dosage form, each dosage containing from about 5 to about 5000 mg, more preferably about 25 to about 3000 mg of the active ingredient. The most preferred unit dosage form contains about 100 to about 2000 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier.

The following examples illustrate the invention.

EXAMPLE 1

Synthesis of (S)-α-methyl-1,3 benzodioxole-5-ethanol 1 equiv. of 3,4-methylenedioxyphenyl acetone, 0.45 equiv. disodium phosphate, 0.03 equiv. phosphoric acid, 12.5 volumes AD-7 resin and 5.8 volumes of water were mixed together and stirred for 15–60 minutes at 20–25° C. 2.27 equiv. of glucose were added and *Z. rouxii* ATCC 14462 is added in an amount of 1.5 grams wet cell paste per gram of ketone (this is 0.375 grams/gram on a dry basis). This mixture was diluted with water to 25 volumes and then gently stirred at 33–35° C. for 8–16 hours. The mixture was filtered on a 100 mesh (~150 micron) stainless steel screen, and the resin which was retained by the screen was washed with 25 volumes of water split into 4 separate portions. The product, which was adsorbed to the resin, was then desorbed from the resin with 25 volumes of acetone. The acetone/product solution was then stripped to dryness under vacuum to yield the title intermediate as a yellow, medium viscosity oil. The in-situ yield was 97–100%, while the isolated yield was 85–90%. The potency was 80–95% and the EE is 100%.

EXAMPLE 2

Synthesis of (5RS,7S)-7,8 dihydro-7-methyl-5-(4-nitrohenyl)-5H-1,3 dioxolo-[4,5-G][2] benzoyran The above intermediate was dissolved ini 4.64 volumes of toluene, filtered over hyflo, and washed with 1.55 volumes of toluene. 1.05 equiv. p-nitro-benzaldehyde and 1.05 equiv. of conc. hydrochloric acid were added, and the mixture was heated to 55–65° C. and stirred 1 hour. A solvent exchange was then conducted at 250 mmHg, replacing the toluene with 12.4 volumes of 93% isopropanol/7% water/ The volume during this solvent exchange varies from 11–14 volumes, and the final volume was ~11 volumes. The mixture was cooled to 0–10° C. and stirred 1 hour. The needle-like product crystals were filtered and washed 2 times with 1.85 vol. isopropanol and dried under vacuum at 50–60° C. The in-situ yield of the title compound was 95+% while the isolated yield was 87–93%. The potency wag 99+% and the RE is 100%.

EXAMPLE 3

Alternative Syntheses of (s)-α-methyl-1,3 benzodioxole-5-ethanol 3.47 grams of 4-bromo-1,2(methylenedioxy)benzene were dissolved in 100 ml of tetrahydrofuran at −78° C., 13.9 ml of 1,3M sec-butyllithium in cyclohexane was then added to consume the aryl halide in less than 30 minutes. 1.00 grams of (S)-(−)-propylene oxide in 2 ml THF was added by syringe and the solution stirred for 45 minutes. The solution was then warmed to 23° C. for 16 hours. The reaction mixture wag poured into 3M ammonium chloride solution and the product isolated by extraction with ethyl acetate. The combined extracts were dried over magnesium sulfate filtered through florisil and concentrated by rotary evaporation. The residual oil was purified by silica gel chromatography and eluted with a 50:50 mixture of hexane and diethyl ether to yield 1.40 g (45%) of the subtitled intermediate. Pchem: [α]365+117.2° (c 1.0, CHCl$_3$) TLC R$^f$=0.26 (50:50 hexane:ether); IR (CHCl$_3$) 3598, 3012, 2973, 2887, 1490, 1249, 1041 cm$^{-1}$; $^{13}$C NMR (CDCl$_3$) d 147.75, 146.19, 132.26, 122.27, 109.68, 108.30; mass spectrum, m/z (FD, M$^+$) 180; Anal. Calcd. for C$_{10}$H$_{12}$O$_3$: C, 66.65; H, 6.71. Found: C, 66.42; H, 6.66.

EXAMPLE 4

Alternative Synthesis of (5RS,7S)-7,8-dihydro-7-methyl-5-(4-nitrophenyl)-5H-1,3-dioxolo-[4,5-G][2] benzopyran 244 grams of p-nitrobenzaldehyde was added to a solution of 300 grams of the intermediate formed in the biocatalyzed reduction step of Example 1 in 4.45 L of toluene. 166.5 mL of concentrated hydrochloric acid was added dropwise over 15–20 min and the resulting mixture was heated to 60° C. for 2.5 h. The mixture was cooled to room temperature and concentrated by rotary evaporation. 3 L of ethanol was added and the mixture was concentrated to a solid. A second 3 L portion of ethanol was added and the mixture was stirred for 1 h. The slurry was cooled overnight and the crystalline product was isolated by vacuum filtration. The filter cake was washed with ethanol and then dried in a vacuum oven at 40–60° C. to yield 450 g (86%) of an off-white solid which was determined to be an isomeric mixture of the above subtitled optically active intermediate. P chem: [a]$^{365+55°}$ (c0.4, CHCl$_3$).

EXAMPLE 5

Synthesis of (5RS,7S)-7,8-dihydro-7-methyl-5-(4-nitrophenyl)-5H-1,3-dioxolo[4,5-G][2]benzoyran-5-ol 350 grams of the isomeric intermediate from Example 4 was added to a solution of 731 mL of dimethylsulfoxide and 2923 mL of dimethylformamide. The mixture was cooled to 8–12° C. and compressed air was passed through the mixture. 117.5 mL of 50% aqueous sodium hydroxide was added in one portion and the resulting mixture was stirred for 4,5 h. The reaction mixture was added by cannula over 30–60 min to 8.25 L of a stirred 1N hydrochloric acid solution at 10–15° C. The resulting precipitate was filtered and washed with 3 L of water then air dried to a constant weight (384 g). The wet cake was carried into Example 6 without further drying. P chem: Data recorded from a 3:1 isomeric mixture. TLC R$_f$=0.19 (75:25 hexane:ethyl acetate); IR (CHCl$_3$) 3605, 3590, 3015, 3000, 2960, 2910, 1608, 1522, 1484, 1352, 1240, 1042 cm$^{-1}$; $^1$H NMR (CDCl$_3$, 300 MHz) d (major isomer) 8.16 (d, 2H, J=6.9 Hz), 7.73 (d, 2H, J=6.9 Hz), 6.55 (s, 1H), 6.38 (s, 1H), 5.86 (s, 1H), 5.83 (s, 1H), 4.38 (M, 1H), 2.70 (m, 2H), 1.39 (d, 3H, J=6.3 Hz); d (minor isomer) 8.27 (d, 2H, J=8.9 Hz), 7.90 (d, 2H, J=8.6 Hz), 6.87 (s, 1H), 6.73 (s, 1H), 6.03 (s, 1H), 6.02 (s, 1H), 3.95 (m, 1H), 2.7 (obscured, m, 2H), 1.24 (d, 3H, J=6.1 Hz); mass spectrum, m/z (FD, M+) 329; Anal. Calcd. for $C_{17}H_{15}NO_6$: C, 62.01; H, 4.59; N, 4.25, found C, 62.22, H, 4.79; N, 4.29.

EXAMPLE 6

Synthesis of (S)-acetic acid-[[6- (2-hydroxypropyl)-1,3-benzodioxol-5-yl](4-nitrohenyl)methylene]hydrazide To 350 g of the wet cake from example 5 in 2300 mL ethanol was added 94.5 g of acetic hydrazide and 1 mL of concentrated hydrochloric acid. The resulting solution was heated to reflux for 2.5 h. The mixture was cooled to room temperature and concentrated to a yellow foam by rotary evaporation. The concentrate was dissolved in 4.9 L of ethyl acetate and washed with 1.5 L of saturated sodium bicarbonate then 1.5 L of brine. The organic phase wag dried over sodium sulfate, filtered and concentrated to give 373 g of a yellow foam (91%). The material was identified as a 1:1 inseparable mixture of isomers of the subtitled compound (97% pure by HPLC). P chem: Data recorded from a 1:1 isomeric mixture. mp 167.8–169.7° C.; TLC $R_f$=0.55 (ethyl acetate); IR ($CHCl_3$) 3590, 3485, 3310, 1694, 1673, 1520, 1485, 1346 cm$^{-1}$; $^1H$ NMR ($CDCl_3$, 300 MHz) d 8.64, 8.50 (s, 1H, NH), 8.18 (d, 2H, Ar-H), 7.74, 7.71 (d, 2H, J=8, Ar-H), 6.99, 6.95 (s, 1H, Ar-H), 6.52, 6.50 (s, 1H, Ar-H), 6.06, 6.05 (d, 2H, J=5, $O_2CH_2$), 2.44 (s, 3H, $CH_3$), 3.87 (m, 1H, CH), 2.4–2.2 (m, 2H, $CH_2$), 1.12, 1.10 (d, 3H, $CH_3$); $^{13}C$ NMR ($CDCl_3$, 75 MHz) d 209.94 (C), 173.38, 173.43 (C), 149.38, 149.62 (C), 148.31, 148.58 (C), 147.90, 148.18 (C), 147.54 (C), 142.5, 143.04 (C), 132.64 (C), 127.53, 127.61 (CH), 123.75, 123.77 (CH), 122.86, 123.27 (C), 112.13 (CH), 110.55 (CH), 108.03, 108.10 (CH), 108.03, 108.10 (CH), 101.83 ($CH_2$), 67.51, 68.08 (CH), 42.37, 42.97 ($CH_2$), 23.48, 23.83 ($CH_3$), 23.48, 23.83 ($CH_3$), 20.47, 20.55 ($CH_3$); $[a]_{589}$+103.8° (c 1, $CHCl_3$); mass spectrum, m/z (FD, M+) 385; Anal. Calcd. for $C_{19}H_{19}N_3O_6$: C, 59.22, H, 4.97N, 10.90. Found: C, 58.99; H, 5.04; N, 10.68.

EXAMPLE 7

Synthesis of (S)-acetic acid[[6-[2-[(methylsufonyl)oxy]propyl]-1,3-benzodioxol-5-yl](4-nitrohenyl)methylene]hydrazide 340 grams of the Example 6 intermediate was dissolved in 2380 mL of methylene chloride. The solution was cooled to 0° to –10° C. and 187 mL of triethylamine was added. 78.2 mL of methanegulfonyl chloride was then added and the resulting mixture was stirred for 15–30 min. 510 mL of water was added. The isolated organic phase was washed with 460 mL of a 1N hydrochloric acid solution and then 500 mL of brine. The methylene choride solution was warmed to 35–450° C. and 4760 mL of hexane was added over 90 min. The mixture was slowly cooled to room temperature and then cooled further to 0–5° C. The product was isolated by vacuum filtration and dried in a vacuum oven at 40–50° C. to give 356.2 grams (87%) of an isomeric mixture of the subtitled compound as a yellow solid. P chem: Data Recorded from a 3:1 isomeric mixture. mp 150.5–152.5° C.; TLC $R_f$=0.80 and 0.73 (ethyl acetate); IR ($CHCl_3$) 1696, 1520, 1486, 1346, 1175, 1041, 923 cm$^{-1}$; $^1H$ NMR ($CDCl_3$, 300 MHz) d 8.44 (s, 1H, NH), 8.20 (d, 2H, J=8.8 Hz, Ar-H), 7.73 (d, 2H, J=8.6 Hz), 6.94 (d, 1H, j=2.7 Hz, Ar-H), 6.57 (d, 1H, 2.6 Hz, Ar-H) 6.08 (d, 2H, J=5.4 Hz), 4.77 (m, 1H, CH), 2.90 (s, 3H, $SCH_3$, major), 2.83 (s, 3H, $SCH_3$, minor), 2.66–2.57 (m, 2H, $CH_2$), 1.30 (d, 3H, $CH_3$, minor), 1.26 (d, 3H, $CH_3$, major); mass spectrum, m/z (FD, M+) 385; Anal. Calcd. for $C_{20}H_{21}N_3O_8S$: C, 51.83; H, 4.57; N, 9.07; S, 6.92. Found: C, 52.05; H, 4.53; N, 8.84; S, 6.96.

EXAMPLE 8

Synthesis of (R)-7-acetyl-8,9-dihydro-8-methyl-5-(4-nitrohenyl)-7H-1,3-dioxolo[4,5-h][2,3]benzodiazepine 325 g of the Example 7 intermediate was dissolved in 3174 mL methanol. To the stirred solution was added 38.1 mL of 50% caustic soda solution. The resulting mixture was stirred for 4 h. 6348 mL of water was added to the mixture and the contents were stirred for 3 h after which period the resulting precipitate was isolated by vacuum filtration. The material was dried in a vacuum oven at 45–55° C. to give 255 grams (97%) of the subtitled compound which was 97.6% pure by HPLC area %. 221 grams of the dried material was further purified by reslurry in 1105 mL of ethanol which was heated to reflux. The resulting mixture was cooled to room temperature and the precipitate was isolated by vacuum filtration. The isolate was dried in a vacuum oven at 45–55° C. to give 199 grams (90%) of the subtitled compound which was 100% pure by HPLC potency assay.

EXAMPLE 9

Synthesis of form IV of (R)-7-acetyl-5-(4-aminohenyl)-8,9-dihydro-8-methyl-7H-1,3-dioxolo[4,5-h][2,3]benzodiazepine To 5 grams of the Example 8 intermediate in 50 mL of ethanol was added 0.5 grams of 10% Pd/C wetted with water. The agitated slurry was treated with a solution of 4 gram of potassium formate in 4 mL of water. The resulting mixture was stirred for 2.5 h and then filtered over Hyflo. The filtrate was concentrated to 10–20 mL by distillation and 22 mL of water was slowly added to the warm (78°) solution. The resulting mixture was heated to 90° C. and then slowly cooled to room temperature. The product was isolated by vacuum filtration and washed with 10–20 mL of water. The isolated solid was dried under vacuum at 50° C. to give 4.17 grams (93%) of the subtitled final compound which was 100% pure by HPLC potency assay. $[\alpha]_{365}$=–303.7 (c=1, methanol).

The product, which was crystalline, was later found to have been Form IV.

EXAMPLE 10

Synthesis of (5RS, 7S)-7,8-dihydro-7-methyl-5-(4-nitrophenyl)-5H-1,3-dioxolo[4,5-G][2]benzopyran-5-ol 15 grams of the Example 4 intermediate (derived from the *Z. rouxii*-mediated ketone reduction) was dissolved in a solution of 75 mL of dimethylsulfoxide and 75 mL of dimethylformamide. The solution was cooled to 7–9° C. and then aereated with 40% oxygen in nitrogen. 7.62 grams of 50% sodium hydroxide in water was added and the resulting mixture was stirred for 3–4 h. The reation was terminated and while maintaining the temperature <12° C., 120 mL of toluene was added followed by a mixture of 45 mL of water and 10 mL hydrochloric acid. The phases were separated and the organic layer was washed with 75 mL of a 10% aqueous sodium thiosulfate solution. The organic layer containing the subtitled intermediate was carried into the next step.

EXAMPLE 11

Synthesis of (S)-acetic acid-[6-(2-hydroxyprolyl)-1,3-benzodioxol-5-yl](4-nitrophenyl)methylenelhydrazide To the toluene solution of the Example 10 intermediate was added 4.26 grams acetic hydrazide and (0.01 volumes)

hydrochloric acid, The resulting mixture was heated to reflux for 3.5 h with removal of water by a Dean-Stark trap. The reaction mixture was concentrated by vacuum distillation to 1 volume. The concentrate was diluted with 105 mL of methylene chloride and washed with 50–55 mL each of saturated sodium bicarbonate solution and brine. The organic solution was dried over magnesium sulfate (0.25 wt. %) and filtered over a hyflo cake. The filter was rinsed with 1 volume of methylene chloride. The combined organic phase containing the subtitled intermediate was carried into the next step.

EXAMPLE 12

Synthesis of (S)-acetic acid[[6-[2-[(methylsufonyl)oxy]propyl]-1,3-benzodioxol-5-yl](4-nitrohenyl)methylene]hydrazide The methylene chloride solution containing the Example 11 intermediate was cooled to 0 to −5° C. and 10 mL of triethylamine was added. 4.1 mL of methanesulfonyl chloride was added slowly to maintain a reaction temperature ≦0° C. 1.5 volumes of water was added to the resulting solution. The organic phase was separated and washed with 2.5 volumes of 1N hydrochloric acid solution. The organic phase was isolated and concentrated to half the original volume by atmospheric distillation. The product was precipitated by the dropwise addition of heptane (2:1 volume heptane to organic concentrate) to the solution at 45° C. The stirred mixture was cooled to 20–25° C. for 1 h, then cooled to 0 to −5° C. for 1–2 h. The precipitate was isolated by vacuum filtration and washed with 3 volumes of 4:1 heptane: methylene chloride then dried in a vacuum oven at 45–50° C. 17.43 grams of the subtitled intermediate (78%) was obtained as an optically active mixture of hydrazone isomers which was 97.7% pure by HPLC potency assay.

EXAMPLE 13

Synthesis of (R)-7-acetyl-8,9-dihydro-8-methyl-5-(4-nitrophenyl)-7H-1,3-dioxolo[4,5-][2,3]benzodiazepine 17.5 grams of the Example 12 intermediate was suspended in 175 mL ethyl alcohol. To the stirred mixture was added 1.7 grams of powdered sodium hydroxide. The resulting mixture was stirred for 1 h. 88 mL of water was added to the mixture and the contents were stirred for 1 h after which period the resulting precipitate wag isolated by vacuum filtration and washed with 175 mL of water. The material was dried in a vacuum oven at 70° C. to give 12.2 grams (86%) of the subtitled compound which was 99.9% pure by HPLC potency assay.

EXAMPLE 14

Synthesis of (R)-7-acetyl-5-(4-aminophenyl)-8,9-dihydro-8-methyl-7H-1,3-dioxolo[4,5h][2,3]-benzodiazepine Using the product of Example 13, the title compound was prepared by an experimental procedure the same as that described in example 9.

EXAMPLE 15

(R)-7-Acetyl-8,9-dihydro-8-methyl-5-(4-nitrophenyl)-7H-1,3-dioxolo[4,5-h][2,3]benzodiazepine 1.05 grams (S)-Acetic acid [[6-[2-[hydroxy]propyl]-1,3-benzodioxol-5-yl](4-nitrophenyl)methylene]hydrazide and 0.78 grams triphenylphosphine in 70 mL tetrahydrofuran were cooled to 0° C. 0.57 grams diethyl azodicarboxylate in 5 mL tetrahydro-furan was added dropwise over 15 min. The resulting mixture was stirred for 2 h then warmed to room temperature for 2 h. The mixture was transferred to a separatory funnel and the solution wag washed with 1N HCl, water and brine. The organic phase was dried over magnesium sulfate, filtered and concentrated by rotary evaporation. The residue was eluted through a silica gel column (1:1 ethyl acetate:hexane). Fractions containing the desired compound were concentrated to a yellow oil which solidified on standing. The yellow crystalline material was slurried in 30 mL of $CH_2Cl_2$ and hexane (3:7) at 0° C. The precipitate was removed by filtration and the filtrate was concentrated to a yellow foam. The residue was suspended in 10 mL ethanol which was warmed to reflux then slowly cooled to room temperature. The precipitate was collected by filtration and dried in a vacuum oven at 60° C. to give 0.51 grams (50%) of the subtitled product (100% ee) which was 98.3% pure by HPLC potency assay.

EXAMPLE 16–18

0.5 ml of frozen yeast suspension containing the microorganism of Table 1 was added to 50 ml of a yeast-malt medium in a 250 ml flask. After 48 hours of shaking, 1.0 ml of culture is added to an additional 50 ml of medium and shaken for 48 more hours. 3,4-methylenedioxyphenyl acetone is added until the final concentration is 10 grams/liter along with 1 ml of 10% glucose. The cultures are incubated and shaken for 24 hours, then analyzed by HPLC for presence of the chiral alcohol intermediate of Example 1.

TABLE 1

| Ex. # | Micro-organism | Source | % Conversion | % EE |
|---|---|---|---|---|
| 16 | Candida famata (C.f.) | A.T.C.C. 26418 | 0.0 | — |
| 17 | zygosaccharoinyces (Z.r.) rouxii | A.T.C.C. 14462 | 77.8 | 99.5 |
| 18 | Mortierrela (M.i.) isobellina | N.R.R.L. 1557 | 1.7 | 94.3 |

EXAMPLE 19

Synthesis of Form I of (R)-7-acetyl-5-(4-aminophenyl)-8,9-dihydro-8-methyl-7H-1,3-dioxolo[4,5-][2,3]benzodiazepine (R)-7-acetyl-8,9-dihydro-8-methyl-5-(4-nitrophenyl)-7H-1,3-dioxolo[4,5-h][2,3]benzodiazepine (38.93 g) was hydrogenated in 730 mL (19 volumes) of 2B-3 ethanol using 7.79 g of 10% palladium on carbon and 1 atmosphere of hydrogen. When HPLC analysis indicated that starting material had been consumed, the catalyst was removed by filtration and the filtrate wag evaporated to afford 38.7 g of crude product. The crude product was dissolved in 220 mL (5.7 volumes) of 1:1 water/ethanol by heating to reflux. The mixture was allowed to cool and the product precipitated near room temperature. The resulting thick, poorly stirring, slurry was stirred at room temperature and then cooled in an ice/water bath. The solid was isolated by filtration and dried in a vacuum oven at 55° C. overnight to afford 31.6 g of purified product. A second recrystallization using the same conditions afforded 28.7 g (80%) of product after drying under vacuum for 3 days at 65° C. and 3 days at room temperature. The product dried very slowly and 1.6% ethanol was still on the sample at this point. Analysis by X-ray diffraction (XRD), solid state NMR (SSNMR) and differential scanning calorimetry (DSC) indicated that the Form I polymorph was formed.

EXAMPLE 20

Synthesis of Form II of (R)-7-acetyl-5-(4-aminophenyl)-8,9-dihydro-8-methyl-7H-1,3-dioxolo[4,5-H][2,3]benzodiazepine (R)-7-acetyl-8,9-dihydro-8-methyl-5-(4-nitrophenyl)-7H-1,3-dioxolo[4,5-H][2,3]benzodiazepine (8.63 g) was hydrogenated in 170 mL (19 volumes) of 2B-3 ethanol using 0.86 g of 10% palladium on carbon and 4.59 g of ammonium carbonate in 5 mL of water as the hydrogen transfer source. When HPLC analysis indicated that starting material had been consumed, the catalyst was removed by filtration and the filtrate was evaporated to afford 8.19 g of crude product. The crude product was dissolved in 50 mL (6.0 volumes) of 1:1 water/ethanol by heating to reflux. The mixture was allowed to cool to room temperature and then cooled in an ice/water bath. The solid was isolated by filtration and dried in a vacuum oven at 60° C. overnight to afford 7.41 g (93%) of purified product. The large crystals contained 5.0% ethanol (GC) and 4.2% water (KF). Analysis by XRD, SSNMR and DSC indicated that the Form II polymorph was formed.

EXAMPLE 21

Synthesis of Form III of (R)-7-acetyl-5-(4-aminophenyl)-8,9-dihydro-8-methyl-7H-1,3-dioxolo[4,5-H][2,3]benzodiazepine (R)-7-acetyl-8,9-dihydro-8-methyl-5-(4-nitrophenyl)-7H-1,3-dioxolo[4,5-h][2,3]benzodiazepine (2.04 g) was hydrogenated in 20 mL (10 volumes ) of 2B-3 ethanol using 0.20 g of 10% palladium on carbon and 1.47 q of potassium formate in 4 mL of water as the hydrogen transfer source. When HPLC analysis indicated that starting material had been consumed, the catalyst was removed by filtration and the filtrate was evaporated to afford 2.09 g of crude product. The crude product was dissolved in 12 mL (6.0 volumes) of 1:1 water/ethanol by heating to reflux. The mixture was allowed to cool and was seeded with Form II crystals at about 40° C. After reaching room temperature, the mixture was cooled in an ice/water bath. The solid was isolated by filtration and dried in a vacuum oven at 50° C. for 24 h to afford 1.45 g (77%) of purified product. Analysis showed 0.05% ethanol (GC) and 0.75% water (KF). Despite using Form II polymorph seed crystals, analysis by XRD, SSNMR and DSC indicated that the Form III polymorph was formed.

EXAMPLE 22

Synthesis of Form IV of (R)-7-acetyl-5-(4-aminohenyl)-8,9-dihydro-8-methyl-7H-1,3-dioxolo[4,5-H][2,3]benzodiazepine (R)-7-acetyl-8,9-dihydro-8-methyl-5-(4-nitrophenyl)-7H-1,3-dioxolo[4,5-h][2,3]benzodiazepine (25.2 g) was hydrogenated in 250 mL (10 volumes) of 2B-3 ethanol using 2.0 g of 10% palladium on carbon and 18.0 g of potassium formate in 20 mL of water as the hydrogen transfer source. When HPLC analysis indicated that starting material had been consumed, the catalyst was removed by filtration. The filtrate was concentrated by distillation until about 70 mL (3 volumes) of ethanol remained. Water (93 mL, 4 volumes) was added to the solution at reflux. The mixture was allowed to cool and was seeded with the crystalline product of Example 9 at 80° C. The resulting slurry was allowed to cool to room temperature and stir overnight. The solid was isolated by filtration and dried in a vacuum oven at 50° C. for 24 h to afford 19.8 g (85%) of purified product. Analysis showed a non-detectable level of ethanol (GC) and 1.0% water (KF).

Analysis by XRD, SSNMR and DSC indicated that the Form IV polymorph was formed.

EXAMPLE 23

Alternative synthesis of (S)-α-methyl-1,3-benzodioxole-5-ethanol

To a suspension of magnesium turnings (17 g) in 50 mL tetrahydrofuran was added dropwise a solution of 5-bromo-1,3-benzodioxole (93.6 g). After complete addition, the mixture was diluted with 250 mL tetrahydrofuran and the resulting mixture was stirred overnight. 13 mL of the solution (0.78 M) was transferred to a round bottom flask containing copper(I) iodide (0.12 g). The resulting mixture was cooled to −50° C. and a solution of (S)-(−)-propylene oxide in 3 mL tetrahydrofuran was slowly added then stirred 10 min. The mixture was diluted with ether. The isolated organic phase was washed with water and brine. The aqueous wash was extracted with ether (2×) and the combined organic solutions were dried over magnesium sulfate, filtered and concentrated. The residue was purified by silica gel chromatography (50% ether in pentane) to give 1.66 g of the desired product (91%). Chiral HPLC analysis indicated that the optical purity of the material was 98.3%.

EXAMPLE 24

Pharmaceutical Formulation

| Active Ingredient | 1 mg | 10 | 50 | 100 |
|---|---|---|---|---|
| Starch | 444.5 mg | 435.8 | 396.2 | 346.6 |
| Silicone fluid | 4.49 mg | 4.22 | 3.84 | 3.36 |

The ingredients were mixed and filled into size 0 hard gelatine capsules to a fill weight of 450 mg.

What is claimed is:

1. A physical form of (R)-7-acetyl-5-(4-aminophenyl)-8,9-dihydro-8-methyl-7H-1,3-dioxolo[4,5-h][2,3]benzodiazepine having an X-ray powder diffraction pattern with d spacings at 12.78, 9.48, 8.99, 8.64, 8.23, 6.39, 6.27, 5.73, 4.01 and 3.96 Å.

2. A pharmaceutical composition, which comprises a physical form of (R)-7-acetyl-5-(4-aminophenyl)-8,9-dihydro-8-methyl-7H-1,3-dioxolo[4,5-h][2,3]benzodiazepine having an X-ray powder diffraction pattern with d spacings at 12.78, 9.48, 8.99, 8.64, 8.23, 6.39, 6.27, 5.73, 4.01 and 3.96 Å and a pharmaceutically acceptable diluent or carrier.

3. A method of blocking AMPA receptors in a mammal requiring such treatment, which comprises administering an effective amount of a physical form of (R)-7-acetyl-5-(4-aminophenyl)-8,9-dihydro-8-methyl-7H-1,3-dioxolo[4,5-H][2,3]benzodiazepine having an X-ray powder diffraction pattern with d spacings at 12.78, 9.48, 8.99, 8.64, 8.23, 6.39, 6.27, 5.73, 4.01 and 3.96 Å.

* * * * *